United States Patent
Haverich et al.

(10) Patent No.: US 6,960,427 B2
(45) Date of Patent: Nov. 1, 2005

(54) PROCESS FOR PRODUCING A VASCULARIZED BIOARTIFICIAL TISSUE AND AN EXPERIMENTAL REACTOR FOR CARRYING OUT THE PROCESS

(75) Inventors: Axel Haverich, Isernhagen (DE); Theo Kofidis, Hannover (DE)

(73) Assignee: Artiss GmbH, Hannover (DE)

( * ) Notice: Subject to any disclaimer, the term of this patent is extended or adjusted under 35 U.S.C. 154(b) by 485 days.

(21) Appl. No.: 10/084,306

(22) Filed: Feb. 28, 2002

(65) Prior Publication Data

US 2002/0081728 A1 Jun. 27, 2002

Related U.S. Application Data

(62) Division of application No. 09/759,638, filed on Jan. 16, 2001, now Pat. No. 6,379,963.

(30) Foreign Application Priority Data

May 4, 2000 (DE) ........................... 100 21 627

(51) Int. Cl.$^7$ ............. C12N 5/06; C12N 5/08; C12N 11/02; C12N 11/08; A61F 2/00

(52) U.S. Cl. ............... 435/1.1; 424/423; 435/177; 435/180; 435/395; 435/399; 435/400; 435/402

(58) Field of Search ............... 435/174, 177, 435/180, 365, 395, 399, 400, 402, 1.1; 424/423, 93.7

(56) References Cited

U.S. PATENT DOCUMENTS

| | | | |
|---|---|---|---|
| 4,908,319 A | | 3/1990 | Smyczek et al. |
| 5,266,480 A | | 11/1993 | Naughton et al. |
| 5,770,417 A | * | 6/1998 | Vacanti et al. ............... 435/180 |
| 5,843,766 A | | 12/1998 | Applegate et al. |

FOREIGN PATENT DOCUMENTS

| | | |
|---|---|---|
| DE | 44 43 902 C1 | 4/1996 |
| DE | 197 11 114 A1 | 9/1998 |
| DE | 197 25 318 A1 | 12/1998 |
| DE | 199 38 518 A1 | 10/2000 |
| WO | WO 91/04317 | 4/1991 |
| WO | WO 95/02037 | 1/1995 |
| WO | WO 97/15655 | 5/1997 |

OTHER PUBLICATIONS

W. Minuth et al., "Organo–typical environment for cultured cells and tissues", *Bioforum*, 17, 1994, 412–416.

R. Carrier et al., "Cardiac tissue engineering: cell seeding, cultivation parameters, and tissue construct characterization", *Biotechnology and Bioengeneering*, 64 (5), 1999, 580–590.

R. K. Li et al., "In vivo survival and function of transplanted rat cardiomyocytes", *Circ. Res.*, 78, 1996, 283–288.

N. Bursac et al., "Cardiac muscle tissue engineering: toward an in vitro an in vivo model for electrophysiological studies" *American Journal of Physiology*, 277 (2), Aug. 1999, H433–H444.

R. K. Li et al., "Survival and function of bioengineered cardiac grafts", *Circulation*, 100, 1999, II–63–II–69.

B. S. Kim et al, "Optimising seeding and culture methods to engineer smooth muscle tissue on biodegradable polymer matrices", *Biotechnology and Bioengineering*, 57 (1), 1998.

* cited by examiner

*Primary Examiner*—David M. Naff
(74) *Attorney, Agent, or Firm*—Witham, Curtis & Christofferson, P.C.

(57) ABSTRACT

The invention concerns a process for producing a three-dimensional bioartificial tissue having viable cells in or on a matrix, and by which cells and matrix can be cultivated into a tissue or a precursor of a tissue, a vascularized tissue of biological materials, obtained by this process, and an experimental reactor for scientific purposes and for producing clinically usable tissues and organs.

9 Claims, 6 Drawing Sheets

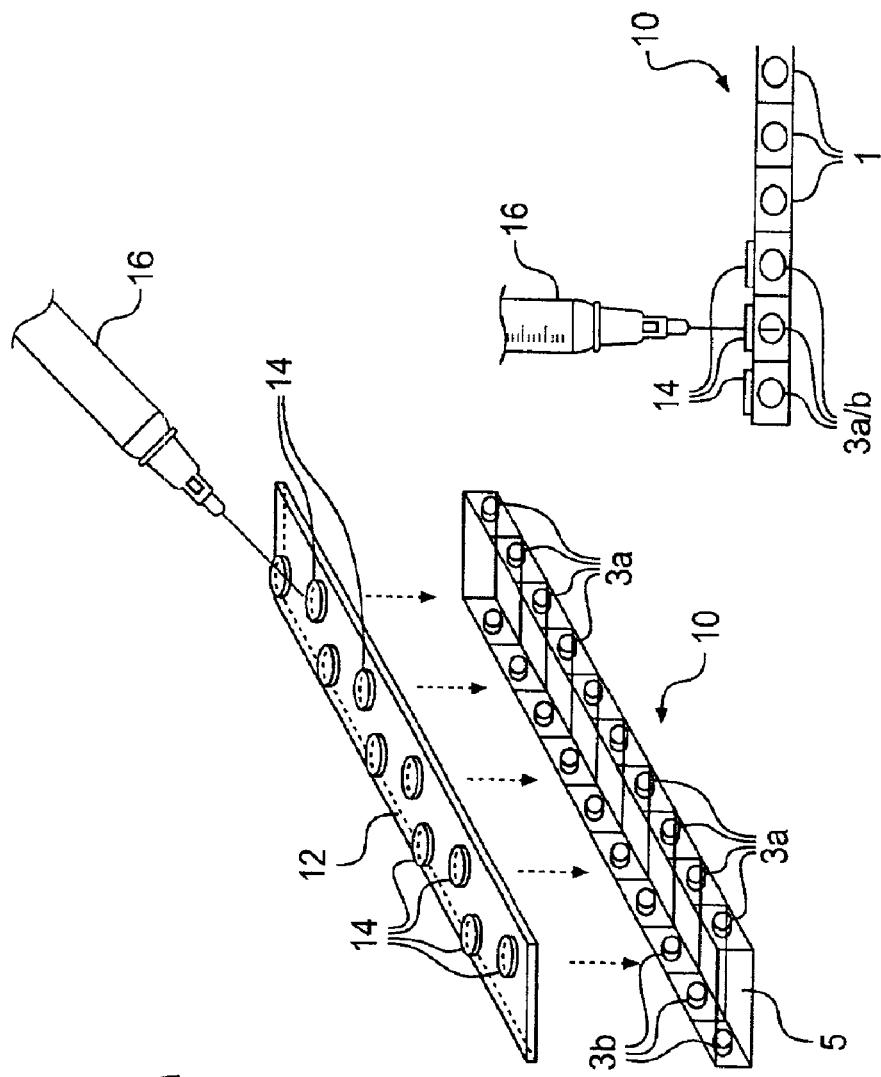

PROCESS FOR PRODUCING A VASCULARIZED BIOARTIFICIAL TISSUE AND AN EXPERIMENTAL REACTOR FOR CARRYING OUT THE PROCESS

RELATED APPLICATION

This application is a divisional of application Ser. No. 09/759,638, filed Jan. 16, 2001 now U.S. Pat. No. 6,379,963, and is incorporated herein by reference.

BACKGROUND OF THE INVENTION

1. Field of the Invention

The invention concerns a process for producing a three-dimensional bioartificial tissue having viable cells in or on a matrix, and by which cells and matrix can be cultivated into a tissue or a precursor of a tissue, a vascularized tissue of biological materials, obtained by this process, and an experimental reactor for scientific purposes and for producing clinically usable tissues and organs.

2. Background Description

Bioartificial tissues are understood to be tissues produced in vitro from natural biological materials, which are, therefore, not natural tissues, but tissues which as nearly as possible simulate natural tissues.

The process according to the invention and the matching reactor are particularly suitable for producing a bioartificial heart muscle tissue.

Morbidity and mortality in the Western population are largely related to loss of heart function and heart tissue (cardiac failure). This is a problem of great socioeconomic relevance. Bypass surgery or heart transplants are increasingly necessary as ultimate therapeutic measures. Transplants, though, involve problems such as lack of suitable donor organs or the stress on transplant patients by lifelong treatment to suppress rejection reactions.

The problems of transplantation affect not only hearts, but also other organs which are no longer functional and which must be replaced. Because of these problems, major attempts have been made in medical research in the areas of "tissue retention" and "tissue and organ replacement". Research endeavors on "tissue and organ replacement" comprise use and better adaptation of xenogeneic organs as well as the culture of three-dimensional tissues from natural starting materials so as to be able to replace at least parts of organs.

In the past, early cellular forms (e.g., embryonal stem cells or infant heart cells) have been injected into recipient myocardium (individually and as clumps of cells).

Prototypes of rat heart muscles in collagen, enriched with nutrients and growth factors have been made to produce, or, initially, to simulate, heart muscle from simple biological basic materials. Contractions have already been demonstrated with them. However, these experiments have not dealt with functional three-dimensional tissue which would be suitable for transplantation and which could replace damaged organ tissue (R. L. Carrier et al., "Cardiac Tissue Engineering: Cell Seeding, Cultivation Parameters and Tissue Construct Characterization", Biotechn. Bioengin. 64 (5), 580–90, 1999).

The artificial pieces of heart tissue so obtained were only a few millimeters thick and never survived longer than a few weeks. After implantation, they were unable to integrate themselves into the recipient tissue so as significantly to improve the strength of beating (B. S. Kim et al., "Optimizing Seeding and Culture Methods to Engineer Smooth Muscle Tissue on Biodegradable Polymer Matrices", Biotechn. Bioengin. 57 (1), 1998; R. K. Li et al., "In vivo Survival and Function of Transplanted Rat Cardiomyocytes", Circ. Res. 1996; 78: 283–288). Thus the objective of the invention is to provide a process for producing an improved three-dimensional bioartificial tissue. In particular, vascularization of the tissue is attempted, so that it can be supplied and thus maintained in a viable state.

SUMMARY OF THE INVENTION

To achieve that objective, the generic concept of the process is designed so that at least one vessel is inserted in the tissue at the beginning of its production. The vessel is supplied from the outside, so that vascular propagation occurs in the course of tissue cultivation and a three-dimensional, vascularized bioartificial tissue is obtained.

Because the tissue is permeated by a vessel even during its cultivation, it can develop three-dimensionally as in nature. The main vessel branches, leading to a vascularized tissue. The vascularized tissue produced can, on transplantation, be connected to the vascular system, so that it remains nourished and viable. There is a more natural modeling of the tissue conditions even during the tissue culture itself. Culturing over longer periods is possible because the supply to alls cells, even those in the interior of the cell assembly, can be better assured. A longer culture can be advantageous, for instance, if a better degree of cell differentiation is to be attained. Culture in the experimental reactor, which is described in more detail below, also allows provision of a physiological environment for organogenesis (e.g., atmospheric pressure or vacuum, defined gas concentrations (partial pressures), biochemical environment, etc.).

A bioartificial tissue in the sense of the invention is understood to be a tissue not taken, as such, from an organism, as by surgery, but rather simulated artificially using biological materials. That is generally done by assembling certain cells into a cell assembly, applying them to a stabilizing substrate, or putting them in a matrix. The substrate or matrix can itself be of synthetic or, alternatively, biological origin. Polymers, especially biodegradable polymers, may be considered as synthetic matrices. They can also be in the form of layers or networks. Collagen in particular is also considered as a matrix material. A segment of tissue, removed from a human or animal, generally acellularized by chemical and/or mechanical methods, can also be used as the source of the collagen matrix.

The bioartificial tissue should contain viable cells so that they can form a three-dimensional biological tissue which has the longest possible stability and viability.

In one simple embodiment, collagen and viable cells can be mixed, and further cultivated (i.e., supplied with a nutrient solution renewed continuously or at intervals). Various simulated tissues have already been recommended and used. The detailed structure of this tissue depends on the nature of the tissue or organ.

The principal problem with tissues comprising biodegradable matrices and cells, especially artificially simulated heart tissue, is their limited dimensions and survivability, because for a long time it has been impossible to nourish them by blood or nutrient medium in a natural manner (see N. Bursac et al., "Cardiac Muscle Tissue Engineering: Toward an in vitro and in vivo model for electrophysiological studies", Am. J. Physiol. 277 (2), HH433-H444, August 1999; R. K. Li et al., "Survival and Function of Bioengineered Cardiac Grafts", Circulation 1999, 100 [Suppl. II]; II-63 to II-69).

The invention is, then, based on the recognition that the ability of a tissue to survive and develop its function is critically dependent on its vascularization (the occurrence of vessels within the tissue). Therefore the process of the invention provides that at least one vessel, which is supplied from the outside, is inserted into the artificial biological tissue at the beginning of its production. By supplying the vessel with a suitable nutrient solution or blood, vessels propagate naturally in the course of the cultivation.

The vessel can be inserted into the matrix, such as an acellularized collagen matrix, before it is inoculated with the cells desired for the artificial biological tissue; or, if the production of the artificial tissue involved only mixing of cells and matrix material, the vessel can be inserted into that mixture at the beginning of the culture.

A vessel of natural origin from a human or animal can be used as the vessel, for instance, rat aortas, especially for scientific experiments. But it can also be an artificial vessel, particularly one of a biologically compatible polymer. It is also possible to use the entire vascular structure of an organ to be supplied.

Preferably, a native vessel with a large lumen, as nearly as possible specific for the species, is used. The extended vessel lumen can have lateral openings or branches. The openings are produced in the simplest case by cutting off side branches from the main branch of a native vessel. On culture of the artificial tissue, vascular development proceeds into the tissue.

Alternatively, an inherently porous vessel can be used. The porosity simplifies the beginning of vascular branching, and could be produced by chemical and/or mechanical treatment of the vessel. The mechanical treatment can also comprise repeated pressure stressing of the vessel, for instance, forcing a pulsing flow through the vessel. If an artificial vessel is used, tubular fiber networks appear particularly suitable. The porosity of the synthetic material can be adjusted as desired by technological means. For instance, a tissue-like synthetic material with freely selectable porosity can be used. The inherently porous vessel can be prepared at points with a material or means providing a stimulus for angiogenesis, such as the protein VEGF (vascular endothelial growth factor).

It is further important for the process that the vessel be supplied, from the inside or outside, with blood or a culture medium. That can be done by perfusing the vessel in the usual manner. That is, it can be connected to a circulatory system of blood or culture medium. Substances promoting angiogenesis, such as VEGF or other known growth factors (TGF, PDGF, VGF) can be added to the culture medium. Such substances, and, in particular, growth factors, can also added directly to the tissue matrix or generally to the tissue mixture.

The perfusion can preferably be done under pressure. In the simplest case, it is provided that the perfusion supply line be of greater diameter than the perfusion drain line, so that a pressure develops within the vessel. Such a pressure is also maintained in very organ in nature, so that perfusion under pressure contributes to simulation of natural conditions. Because of the pressure, liquid is forced into the tissue, resulting in a mechanical stimulus that promotes vascular development. Perfusion under pressure can also be accomplished in other ways with suitable pumps and throttling elements.

It is considered particularly advantageous for the perfusion to be pulsatile, as this most nearly approaches a natural supply of the tissue, pulsing with the heart beat.

The technological realization of pulsatile perfusion, under more or less pressure, is basically known at the state of the art, and therefore need not be described in further detail here.

With the supply and drain lines needed for the perfusion, the vessel can also be positioned and fixed within the tissue. That applies particularly for tissue cultures of gel-like mixtures.

In one preferred embodiment, cardiomyocytes are used as cells within the tissue to be artificially vascularized, so as to give an artificial heart tissue. The principle of vascular development is also applicable to other bioartificial tissues, though, particularly to skin tissue. In the latter case, keratinocytes are used preferably as cells.

Kidney tissue, lung tissue, and other tissues can be obtained in corresponding ways. Complete bioartificial organs (heart, kidney, lung) can be obtained by specifying the geometric form of the culture and inserting a vascular tree for an entire organ.

By means of the invention, it is possible for the first time to obtain a vascularized three-dimensional tissue distinguished by the fact that at least one vessel passes through it, from which other vessels branch off into the tissue. The vascularized transplants can be integrated better into the receiving bodies, as they can be supplied continuously from the beginning. When the tissue is used as a transplant, the vessels of the artificial biological tissue can be connected with the vascular system of the receiver's own body, so as to assure immediate supply of the newly inserted tissue. For artificial heart tissue, there are the particular advantages that the tissue segments can, for the first time, exceed a thickness of a few millimeters and that the survivability of the vascularized, three-dimensional tissue is distinctly superior to that of a non-vascularized tissue.

The invention also covers an experimental reactor for controlled production of an artificial biological tissue, particularly by the process of the invention for producing a vascularized artificial tissue. This experimental reactor is characterized by at least one tissue culture chamber, at least one inlet and outlet for this, or each, chamber, and by two opposite plane, parallel and optically transparent boundary walls of this or of each tissue culture chamber. The experimental reactor is particularly intended for making biological and physiological research on bioartificial tissues easier. For that purpose, the reactor is designed so that the contents of the culture chamber can be examined and observed by optical procedures. The reactor can be exposed directly to optical methods of examination during the culture process by means of the two or more [see Note 1] opposite plane, parallel and optically transparent boundary walls. The contents of the reactor culture chamber(s) can be observed directly with a microscope; and still or motion pictures can be made of the contents.

With multiple separate tissue culture chambers, serial investigations can be carried out with variation of certain parameters, so that research on bioartificial tissues can also be distinctly systematized and made easier. There are many possibilities in the suggested experimental reactor for influencing the culture process and applying various growth-promoting measures. The blood and nutrient supply of the bioartificial tissue can be observed well and optimized by varying different parameters.

In this way the experimental reactor is simply designed and economical to produce. The experimental reactor is preferably provided with at lest one closable inlet and outlet per chamber. The preferred closure means comprise cocks, valves, hose clamps, and/or diaphragms. The inlets and outlets can at the same time serve to delimit and fix the vessels to be positioned within the tissue culture in the process according to the invention. However, separate means can also exist for fixing the vessels, such as means for fixing an extracellular matrix, such as an acellularized collagen substrate.

One of the plane, optically transparent boundary walls of the chamber can preferably be made as a lid. It is advantageous to provide at least one additional closable inlet, or an addition point for each chamber to influence the medium or the substrate. These can, for instance, be supports with threaded connections, with diaphragms inserted in the screw holes [see Note 2]. Certain substances which can affect the development of the artificial tissue in the culture can be added through these addition sites with a syringe (see above, e.g., VEGF).

The reactor inlets or outlets are preferably connected to a micropump and a tubing system through which blood or nutrient medium is provided. The drain line or lines is/are preferably connected to a waste tank.

BRIEF DESCRIPTION OF THE DRAWINGS

The foregoing and other objects, aspects and advantages will be better understood from the following detailed description of a preferred embodiment of the invention with reference to the drawings, in which:

FIGS. 6A-6B show the example embodiment of FIG. 5 with a different lid which also has addition points closed with diaphragms.

DETAILED DESCRIPTION OF A PREFERRED EMBODIMENT OF THE INVENTION

The invention is explained in more detail in the following by means of drawings which show one embodiment of the experimental reactor according to the invention, and by means of which an example embodiment is also explained for carrying out the process for producing a bioartificial heart tissue.

FIG. 1 shows an experimental reactor, designated as a whole as 10, of ten rectangular tissue culture chambers 1 laid in parallel.

Figure 1C:
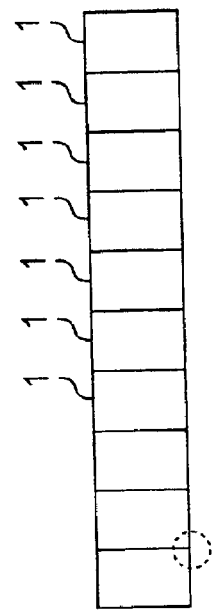
FIGS. 1A-1D are a schematic representation of one example embodiment of the experimental reactor with ten tissue culture chambers in parallel, in a perspective view (a), in a top view from the narrow side (b), in a top view from above (c), and from above in detail (d).
Figure 1D:
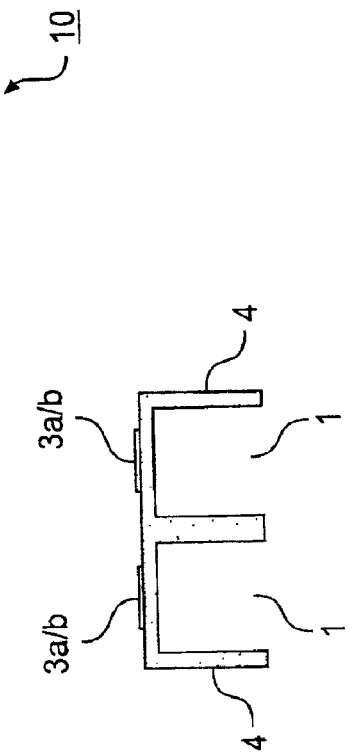
Figure 1A:
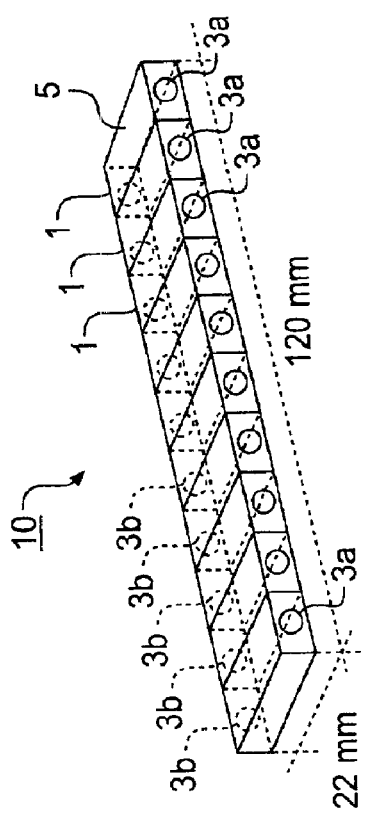
Figure 1B:
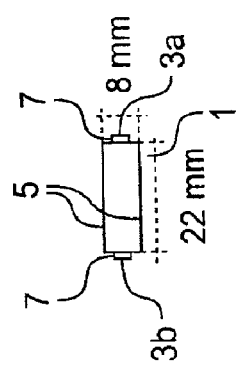

The entire reactor 10 is made up as a block and in this example embodiment is of glass. The total length of the ten tissue culture chambers here is about 120 mm. The width is 22 mm and the height is 8 mm. The width of 22 mm corresponds to the length of an individual tissue culture chamber, through which there is flow from the inlet 3a to the outlet 3b. The side view of a single tissue culture chamber, or the front view of reactor 10 as a whole, is shown in more detail in FIG. b. FIG. 1c shows a top view of the block-like reactor with the individual chambers 1. FIG. 1d shows a detail of this drawing. From that, it can be seen how the individual chambers are provided with a silicone cover 4. In this example, the inner surfaces of the chambers 1, as well as the interiors of the inlets and outlets 3a, 3b, are coated with silicone, which is biocompatible and which does not adhere to tissue.

It is critical for the observability of the substrate during the culture that the upper and lower boundary walls 5 of the chambers, that is, the top and bottom of the reactor 10, are plane and parallel to each other, and are made of an optically transparent material, such as glass, in this case. The side walls of the reactor can, on the other hand, be of plastic, for instance, directly of silicone. This embodiment of the invention, with the plane boundary walls 5, makes it possible to carry out optical examinations directly on the reactor during culture, for instance, microscopic observation, photography, or filming.

Figure 2:
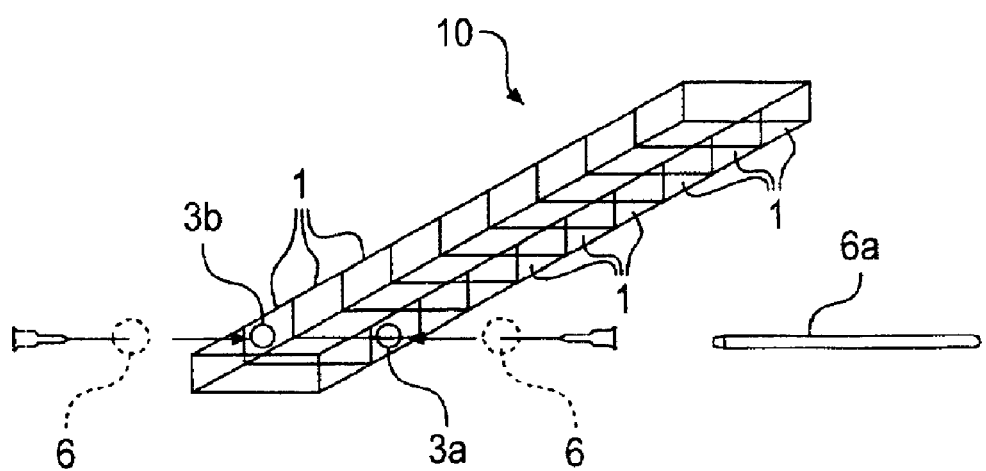
FIG. 2 shows a simplified schematic representation of the reactor shown in FIG. 1 with the possibilities for connecting inlets and outlets.

FIG. 2 shows a corresponding experimental reactor 10, again with 10 tissue culture chambers, in a simplified schematic representation. For simplicity, not all the inlets and outlets, 3a, 3b, are shown. The inlets and outlets of the individual tissue chambers, 3a and 3b, are, for simplicity, shown here for only one of the chambers. They are sealed off with silicone in this example embodiment, though they can also be closed off with ordinary diaphragms. The arrow in FIG. 2 indicates how the usual needle tips 6 are introduced. These needle tips 6 are connected with tubing systems to supply and drain nutrient solutions or blood. Detail 6a shows a ground-off canula tip such as can be used advantageously for introducing and removing medium. Canulas of various thicknesses are used preferably, so that in this way, as described above, a pressure can be developed in the vessel between the canulas if the input is through the larger canula and the drain through the smaller one. (Sizes 18 and 21 gauge in this example.)

Figure 3:
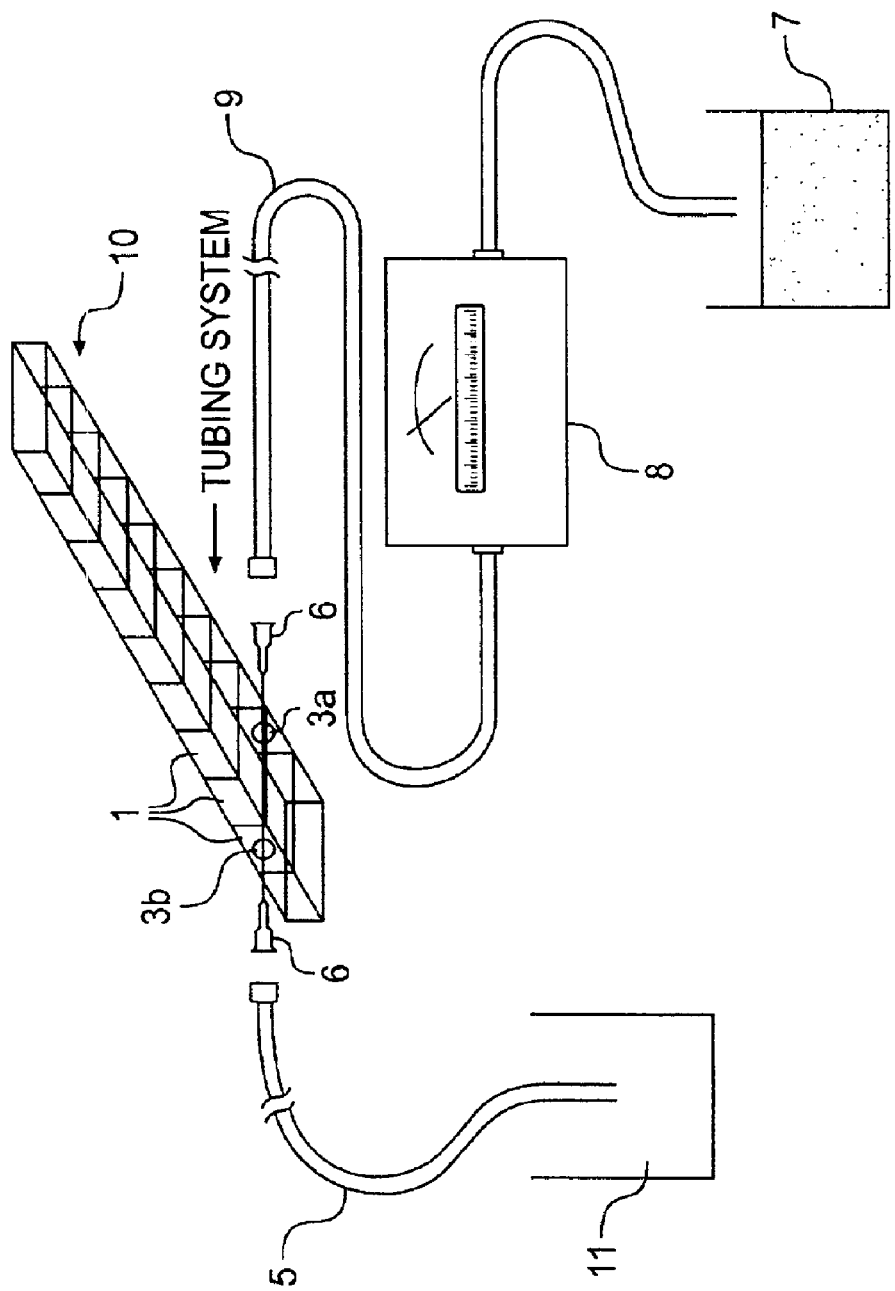
FIG. 3 shows schematically the feed for the inlets and outlets of the example embodiment presented in FIGS. 1 and 2.

FIG. 3 shows the corresponding example embodiment in which the needle tips with the canula tips are passed through the silicone seals of the feed and drain lines 3a, 3b. To simplify the drawing, the other connections were omitted, just in the drawing. In the example embodiment shown, all the tissue culture chambers 1 are connected in parallel in the same manner with the culture medium supply reservoir 7, pump 8, tubing system 9 and waste tank 11.

Figure 4:
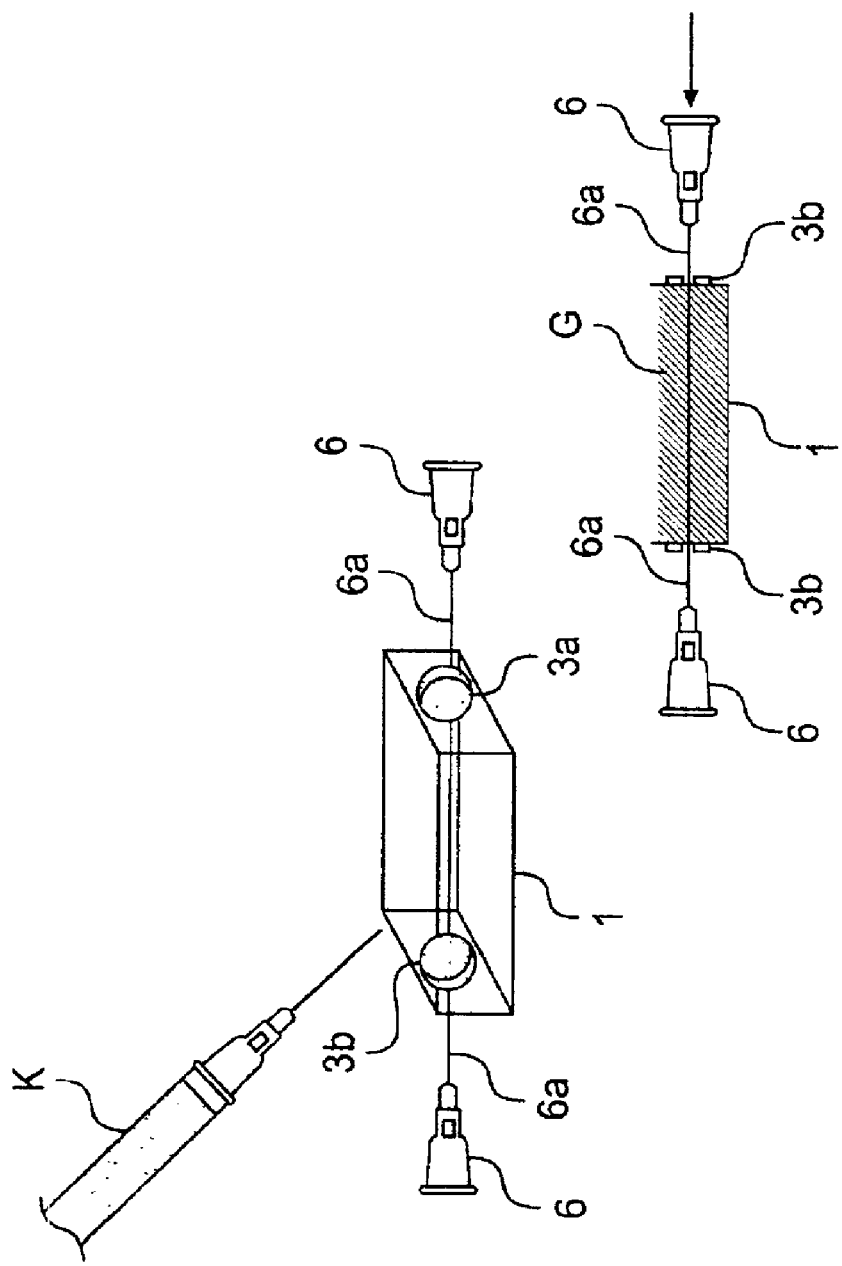
FIG. 4 is a schematic representation of an individual tissue culture chamber with a vessel held inside it.

FIG. 4 shows a longitudinal section through a single tissue chamber along a vessel G held between inlet and outlet 3a and 3b. Corresponding parts are marked with corresponding reference numbers. The vessel G is pulled over the canulas 6a of the needle tip 6, which are passed through the seals of the inlet and outlet, 3a and 3b. In this way it is both held and positioned within the tissue culture chamber so that it is about in the center of the mixture of cells and Matrigel [see note 4] filling the chamber. Perfusion is done, again, as shown in FIG. 3.

FIG. 4 also shows a perspective view of the same chamber which is open at the top, like a Petri dish and can be coated with the mixture K of the starting materials for the artificial tissue with a simple syringe. Then the chamber can be closed with a lid, as shown in FIG. 5.

Figure 5:
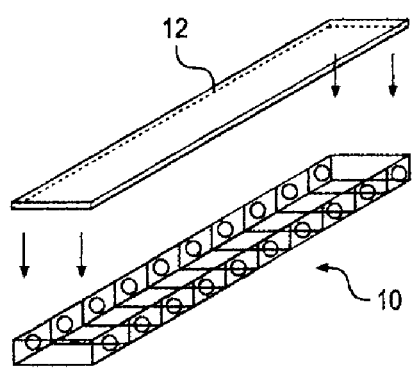
FIG. 5 shows the design of an experimental reactor with ten tissue culture chambers having a common cover, in a perspective view.

FIG. 5 shows the experimental reactor 10 in the same embodiment as in FIGS. 1 to 4, except in a simplified presentation in an exploded view. It can be seen from the figure how the block-shaped reactor body, made up of the ten individual culture chambers 1, can be combined with a removable lid 12. Although the culture can also be carried out in an open reactor, depending on the desired tissue, as for a Petri dish, the lid 12 is provided as a cover for microscopy and for transport. In general, the lid protects the culture from contaminants. The lid 12 is parallel to the base of the reactor 10. Both surfaces are plane and optical and transparent [see Note 3] so that spectroscopic examinations, photography, microscopy, or simple observation of the culture can be done directly within this closed protected container.

FIG. 6 shows the reactor of the example embodiment described previously, with ten individual culture chambers, in an exploded view with a different cover 12 (culture lid), which has screw connections above each of the individual chambers, closed with diaphragms 14 mounted in the screw holes. Certain substances such as growth factors or medium additives can be added separately through these additional inlets or feed points, so that deliberate variation of the culture conditions in a series of experiments in reactor 10 is possible. FIG. 6a shows an exploded perspective view of this reactor. FIG. 6b shows the same reactor in the closed state, in a side view. The syringe 16 is intended to indicate how certain substances can be added to the individual tissue culture chambers.

The experimental reactor according to the invention has the following principal advantages:

1. It is the first bioreactor usable as a heart muscle bioreactor, and acts not only as a culture chamber but also simultaneously can simulate natural dynamic processes, such as blood supply through elastic pulsing vessels, and pressure changes. These pressure changes occur similarly in living organisms and have critical effects on the development of the tissue culture (flow, pressure gradient, osmosis, diapedesis, shear stress).
2. It is the first bioreactor which can be operated so simply under sterile conditions and which can be manipulated in various ways. It is particularly advantageous that the reactor, because of its plane and parallel boundary surfaces, can be placed on a standard microscope and the cultivation experiment can be documented in any intermediate phase.
3. Due to the additional input points, preferably in the lid, it allows numerous applications of various substances during any phase of the experiment.
4. The design of the experimental reactor with multiple chambers allows modular comparison studies in an experimental series, in which certain parameters can be held constant. This can substantially reduce the labor cost for experimental series, so that the net rate of the work is increased. The reactor makes it possible to carry out experimental series with many degrees of freedom and variables. Different media can be pumped through the individual chambers; the composition of a basal medium can be varied in the different chambers; certain substances can be added only to individual chambers; or a concentration gradient of the same substance can be applied across the number of chambers. The perfusion of the vessels in the culture chambers can be varied physically across broad ranges, for instance, by pulsatile or non-pulsatile flow and by varying the flow rate. Finally, additional electrical stimulation of the cells can be accomplished by electrical stimulation of the culture through electrical contacts in the individual chambers.
5. The flat construction and parallel connection of the chambers makes it possible for multiple experimental reactors to be stacked, so that a complex culture and perfusion system can be built up of multiple modules.
6. The size and construction principle are such that the construction cost remains small, and in that way the reactor can be built and put into operation quickly.

Example of the Process for a Scientific Experimental Series

Neonatal rat muscle hearts were obtained by established enzymatic methods from our own breeding. While the cells were being prepared for culture, freshly obtained rat aortas were fastened between the canulas inside the experimental reactor and connected to a micropump. A medium reservoir was connected in series with them. After the cells were prepared and purified, they were poured into Matrigel [see note 4] and the mixture was loaded into each individual chamber. Two hours later, after the cell-gel mixture had become solid, the pump was started. The mixture obtains a constant mechanical, nutritious, and migrative stimulus (initiating cell migration) through the holes of the cut-off aortal branches. This stimulates the propagation of microtubular structures from the fastened aorta into the mixture. That can be observed under a microscope. In an initial cultures series, culture medium containing 5% $O_2$ was pumped through the vessel. One hour after beginning of the perfusion, the protein VEGF (a factor promoting vascular propagation) was administered through the lid diaphragms of half of the chambers. The other chambers were only perfused. The administration of VEGF was repeated daily.

After perfusion for 7 days, the solid tissue was removed with the vessel and fixed in glutaraidehyde. Multiple slices were stained by HE [see note 5] and immunohistochemical staining to detect troponin and tropomyosin, and also to determine lactate and glucose concentrations at various distances from the aortal vessel running through the center. EHTs [see note 5] simply perfused were compared with those treated with growth factor with respect to cell vitality, metabolic activity and abundance of vessels. In the next step of the research, another vascular propagation stimulator can be tested, and the $O_2$ concentration can be altered. The fixation in each case is done after time intervals of different lengths so identify the parameters which produce the best possible cell vitality and the highest vascular growth.

What is claimed is:

1. A vascularized bioartificial tissue for implantation, made by the process of:

inserting at least one vascularizing vessel into a mixture of viable cells in or on a matrix whereby the at least one vessel is inserted prior to or at the beginning of cultivation of the mixture of the matrix and cells; and cultivating said mixture wherein the at least one vessel propagates and a vascularized bioartificial tissue is obtained, and wherein said step of cultivating includes supplying constituents to said at least one vessel from a location remote from said tissue.

2. The vascularized bioartificial tissue of claim 1, wherein said process further comprises the step of providing a mechanical, nutritious or migrative stimulus to said mixture during cultivation.

3. The vascularized bioartificial tissue of claim 1, wherein said at least one vessel contains branches.

4. The vascularized bioartificial tissue of claim 1, wherein said at least one vessel contains lateral openings.

5. The vascularized bioartificial tissue of claim 1, wherein said at least one vessel is inherently porous.

6. Vascularized bioartificial tissue according to claim 1, wherein the at least one vessel passes through said tissue and other vessels are propagated into the tissue from the at least one vessel.

7. Vascularized bioartificial tissue according to claim 6 wherein the at least one vessel is selected from the group consisting of a vessel of natural origin from human or animal, and a biocompatible synthetic vessel.

8. Vascularized bioartificial tissue according to claim 6 wherein the tissue is a synthetic bioartificial heart tissue having cardiomyocytes in the matrix.

9. Vascularized bioartificial tissue according to claim 6 wherein the tissue is bioartificial skin tissue having keratinocytes in the matrix.

* * * * *